US009849259B2

(12) United States Patent
Colman et al.

(10) Patent No.: US 9,849,259 B2
(45) Date of Patent: Dec. 26, 2017

(54) ENDOSCOPIC BITE BLOCK

(75) Inventors: Joshua Lewis Colman, Jerusalem (IL);
Gershon Levitsky, Jerusalem (IL);
Kathleen Niebel, Westminster, MA (US)

(73) Assignee: ORIDION MEDICAL 1987 LTD., Har-Hotzvim (IL)

( * ) Notice: Subject to any disclaimer, the term of this patent is extended or adjusted under 35 U.S.C. 154(b) by 297 days.

(21) Appl. No.: 12/744,647

(22) PCT Filed: Nov. 25, 2007

(86) PCT No.: PCT/IL2007/001451
§ 371 (c)(1),
(2), (4) Date: May 25, 2010

(87) PCT Pub. No.: WO2009/066277
PCT Pub. Date: May 28, 2009

(65) Prior Publication Data
US 2010/0262033 A1    Oct. 14, 2010

(51) Int. Cl.
A61B 5/097    (2006.01)
A61M 16/04    (2006.01)
A61M 16/06    (2006.01)
A61M 16/08    (2006.01)
A61M 16/10    (2006.01)
(Continued)

(52) U.S. Cl.
CPC ..... *A61M 16/0493* (2014.02); *A61B 1/00154* (2013.01); *A61B 5/0836* (2013.01); *A61B 5/097* (2013.01); *A61M 16/0488* (2013.01); *A61M 16/0497* (2013.01); *A61M 16/0672* (2014.02); *A61M 16/085* (2014.02); *A61M 16/1005* (2014.02); *A61M 16/20* (2013.01);
(Continued)

(58) Field of Classification Search
USPC ............ 600/532; 128/206.26, 569, 861, 862, 128/204.22, 204.23, 205.23, 207.14
See application file for complete search history.

(56) References Cited

U.S. PATENT DOCUMENTS 3,452,366 A    7/1969  Downey
4,446,869 A    5/1984  Knodle
(Continued)

FOREIGN PATENT DOCUMENTS

EP    0190388 A2    8/1986
GB    2173105    10/1986
(Continued)

OTHER PUBLICATIONS

ISR of PCT/IL07/01451 dated Dec. 9, 2008 (5 pages).
European Search Report Application No. 12858318.4 Completed; Aug. 24, 2015; dated Sep. 2, 2015 6 Pages.

*Primary Examiner* — Christian Jang
*Assistant Examiner* — Michael Catina
(74) *Attorney, Agent, or Firm* — Fletcher Yoder PC

(57) ABSTRACT

There is provided herein, a bite block (100) comprising an insertion channel (134) and an airway channel (132) wherein the airway channel is adapted to receive exhaled breath and wherein the first insert channel is adapted to pass a medical instrument. There is provided herein, a bite block comprising an oral insert channel, wherein a portion of said channel opens into a cavity (142) adapted to slidably receive an oral prong (270) the oral insert channel is adapted to receive exhaled breath.

18 Claims, 5 Drawing Sheets

(51) Int. Cl.
*A61B 1/00* (2006.01)
*A61B 5/083* (2006.01)
*A61M 16/20* (2006.01)

(52) U.S. Cl.
CPC .. *A61B 2505/05* (2013.01); *A61M 2202/0208* (2013.01); *A61M 2210/0637* (2013.01)

(56) References Cited

U.S. PATENT DOCUMENTS

| | | | |
|---|---|---|---|
| 4,495,945 A | | 1/1985 | Liegner |
| 4,848,331 A | * | 7/1989 | Northway-Meyer ............... A61M 16/0488 128/200.26 |
| 5,273,032 A | * | 12/1993 | Borody .................... 128/207.14 |
| 5,291,882 A | * | 3/1994 | Makhoul et al. ......... 128/207.14 |
| 5,413,095 A | * | 5/1995 | Weaver ................... 128/200.26 |
| 5,513,634 A | | 5/1996 | Jackson |
| 6,063,062 A | | 5/2000 | Paradis |
| 6,089,541 A | | 7/2000 | Weinheimer et al. |
| 6,098,617 A | * | 8/2000 | Connell .................. 128/200.26 |
| 6,437,316 B1 | | 8/2002 | Colman et al. |
| 8,123,727 B2 | | 2/2012 | Luther et al. |
| 2004/0103896 A1 | * | 6/2004 | Jafari et al. ............... 128/204.18 |
| 2004/0129273 A1 | * | 7/2004 | Hickle ..................... 128/207.14 |
| 2005/0087715 A1 | | 4/2005 | Doyle |
| 2006/0042631 A1 | * | 3/2006 | Martin et al. ............ 128/207.18 |
| 2006/0042638 A1 | | 3/2006 | Niklewski |
| 2006/0278238 A1 | * | 12/2006 | Borody ......................... 128/848 |
| 2007/0006878 A1 | * | 1/2007 | Mackey et al. ........... 128/200.26 |
| 2007/0277823 A1 | * | 12/2007 | Al-Ali et al. ............. 128/204.18 |
| 2008/0053434 A1 | * | 3/2008 | Wightman et al. ...... 128/200.26 |
| 2008/0110456 A1 | * | 5/2008 | Flynn et al. .............. 128/200.26 |
| 2008/0265191 A1 | | 10/2008 | Walborn |
| 2008/0295849 A1 | * | 12/2008 | Reynolds et al. ............. 128/859 |
| 2009/0013995 A1 | * | 1/2009 | Williams .................. 128/200.26 |
| 2010/0101567 A1 | * | 4/2010 | Hauge ..................... 128/200.26 |
| 2010/0132700 A1 | * | 6/2010 | Filipi et al. .............. 128/200.26 |

FOREIGN PATENT DOCUMENTS

| | | |
|---|---|---|
| WO | 2005/016142 | 2/2005 |
| WO | 2007/061609 | 5/2007 |
| WO | 2007/063532 | 6/2007 |
| WO | 2007/081050 | 7/2007 |
| WO | 2008144513 A1 | 11/2008 |
| WO | 2008/151180 | 12/2008 |

* cited by examiner

ENDOSCOPIC BITE BLOCK

FIELD

The invention relates to medical appliances.

BACKGROUND

Numerous medical procedures require the insertion of an instrument, such as an endoscope, down a person's mouth and into the body. Such is the case when performing, for example, an Esophagogastroduodenoscopy (EGD), a procedure comprising the insertion of a flexible endoscope through the mouth until reaching the duodenum (first and shortest part of the small intestine). The endoscope when inserted is used to provide a visual inspection of the organs, and optionally to perform medical procedures such as, for example, biopsies, incisions, and retrieval of foreign objects.

Endoscopic procedures are usually performed while a patient is under topical or moderate sedation, although in some circumstances it may be performed while the patient is under general anesthesia. During moderate sedation or general anesthesia the patient is generally sedated intravenously to minimize gagging and to facilitate the procedure. A bite block is used to prevent the patient from biting on the endoscope, to facilitate the introduction of the endoscope into the mouth, and to maneuver the endoscope relatively freely while inserted in the mouth.

A frequent occurrence when administering intravenous sedation is reduced breathing in the patient, which may lead to hypoxia, or a reduction of oxygen in the blood. It is then substantially common practice to administer oxygen or another breathable gas to the patient, usually through a nasal cannula, while the patient is sedated. Additionally, the patient's exhaled breath is typically monitored, by means of a capnograph, in order to corroborate that the patient's carbon dioxide levels in the blood and the tissues are within safe limits.

A number of bite blocks have been adapted with features to supply oxygen, or optionally some other type of breathable gas, to a sedated patient. Some have been further adapted with features which allow the patient to be connected to a capnograph for measuring the carbon dioxide contents in the patient's exhaled breath. The following patents and/or publications describe different types of bite blocks adapted with some of these features, all of which are incorporated herein by reference.

U.S. Pat. No. 5,273,032 "Oxygenating Oral Medical Appliance", describes an "endoscopic mouth guard having a smoothly contoured, waisted tube merging into a peripheral flange at the front end of said tube, a manifold integral with the front face of said flange defining a closed ended, transverse distribution duct, and two open ended, upwardly directed branch ducts ending, in use, closely below the nostrils of a patient fitted with the guard, two further, open ended branch ducts extending rearwardly from said distributor duct into the bore of said tube, and a laterally and rearwardly directed tapered spigot on said manifold, defining an extension of said distributor duct, adapted to enter the bore of a gas supply tube. The finished guard is a single article of plastics material having a smooth hard surface."

U.S. Pat. No. 5,513,634 "Combination Integral Bite Block Airway and Nasal Cannula", describes a "combination plastic relatively rigid bite block and soft nasal cannula intended for one-time use for supplying oxygen to a patient's nostrils during an endoscopic procedure. The cannula is fixed into the bite block by an integral clip portion of the cannula extending downwardly from a manifold portion and adhered to the bite block. Flexible nasal prongs extend upwardly from the manifold into the patient's nostrils to supply supplementary gas separately from air breathed through the patient's mouth."

US Patent Application Publication No. US 2007/0006878 A1 "Capnographic-oxygenating Oro-fiberscopic Bite block", describes an oro-fiberscopic bite block. "The bite block is utilized during oral fiberscopic procedures. The bite block includes a main structure having an orifice sized to accommodate entry of a fiberscope, such as an endoscope, through the orifice. The bite block includes an extension extending inward from the main structure when positioned within the mouth of a patient. On each side of the orifice is a loop for handling and positioning the bite block within the patient's mouth. The bite block includes an exhalation tube running from the extension to a monitoring device which allows monitoring of the patient's expelled gases. In addition, an inhalation tube may be used to provide supplemental oxygen to the patient. The bite block is positioned in the mouth of the patient with the mouth of the patient surrounding the extension. The tubes include openings which are located on the extension and lie in the interior of the mouth to provide monitoring of uncontaminated gasses expelled by the patient."

PCT International Application Publication No. WO 2007/063532 "Endoscopic Bite Block", describes a "bite block assembly adapted for capnography and oxygen delivery to a subject, the bite block assembly including a first capnography passageway adapted for passage therethrough of exhaled breath from the subject to a capnograph and a second oxygen delivery passageway, separate from the first passageway, adapted for passage therethrough of oxygen from an oxygen source to the mouth of the subject."

There is still a need in the art for improved bite blocks, systems including them and methods that would allow efficient breath sampling during medical procedures such as endoscopy.

SUMMARY

An aspect of some embodiments of the invention relates to a device, such as a bite block device, a system, such as a bite block and an oral nasal breath sampling cannula, and method for sampling breath, for example for the purpose of capnographic measurements, while performing a medical procedure such as insertion of an endoscope. In addition, the device may also include oxygen delivery element(s).

Since experience has shown that patients have a tendency to breath through their mouth during a procedure such as endoscopy, according to some embodiments, the device, system and method provide oxygen delivery and oxygen flow regulation means that facilitate the direction of the oxygen flow to the mouth and/or to the nose as needed and/or when needed. For example, when the bite block is in place the system is adapted to provide more oxygen to the mouth or even, only to the mouth. However, when the bite block is not in a patient's mouth the system is adapted to provide more oxygen to the nose or even, only to the nose. In addition, in many of the existing bite blocks adapted to deliver oxygen and allow capnographic measurements, problems have been encountered associated with the oxygen being delivered at a relatively higher pressure than that at which the exhaled breath is expelled by the patient. The higher pressure, at which the oxygen is delivered orally and/or nasally, occasionally forces the exhaled breath away from an entrance to exhaled breath collection means or allows oxygen into the sampling tubes. For example, when a patient is lightly breathing through the nose or not breathing through the nose at all, during endoscopy or due to any other reason, the collection of the exhaled breath may be diluted with the supplied oxygen, which affects the accuracy of the capnographic measurements. Another example may be during medical procedures known as MAC, monitoring anesthesia care, where U.E. procedures are performed using high levels of oxygen, typically in excess of 5 l/min. According to some embodiments, the device, system and method are adapted to improve breath sampling and to reduce dilution of the sampled breath with oxygen. Furthermore, thedevice, system and method are adapted to provide high oxygen delivery, optionally at rates up to 10 L/min.

According to an aspect of some embodiments of the invention, orally delivered oxygen or optionally, any other breathable gas, delivered at a relatively high pressure, is substantially prevented from interfering with the free flow of orally exhaled breath, by separately channeling the oxygen through an oxygen channel and the exhaled breath through an airway channel, and by maintaining a substantial distance between the openings to these channels. The pressure of the oxygen at an opening of the airway channel is less than the pressure of the opposing exhaled breath and therefore, oxygen is substantially prevented from entering the airway channel and diluting the exhaled breath. Additionally, the oxygen channel may include a relatively large aperture at one end through which the oxygen flows from the oxygen channel into the back of the patient's mouth. The use of a relatively large aperture causes a pressure decrease in the flow of oxygen when exiting from the oxygen channel. Optionally, more than one oxygen channels may be used. Additionally or alternatively, the oxygen channel or channels may include several apertures. The distance between the two channel openings may be determined by the pressure at which the oxygen exits the oxygen channel in the bite block. For example, the airway channel may be designed to extend inwardly to the direction of the mouth of the patient relative to the oxygen channel. Optionally, the oxygen channel may be designed such that the oxygen flow is not directly in the direction into the back of the mouth of the patient, for example, slanted downwards. In this manner, an efficient collection of exhaled breath for capnographic measurements may be maintained while substantially high oxygen delivery is performed. In some embodiments of the invention, the oxygen channel may comprise one or more apertures in the insertion channel through which oxygen, or optionally a portion of the delivered oxygen, may flow out of the oxygen channel into the patient's mouth.

In accordance with some embodiments of the invention, there is provided a bite block including an insertion channel through which a medical instrument, for example, an endoscope, may be inserted into the mouth of the patient. The bite block may further include an airway channel, which extends further into the mouth of the patient relative to the oxygen channel and to the insertion channel. In some embodiments of the invention, an opening may extend partially or entirely, along the length between the airway channel and the insertion channel. The bite block may also include an oxygen channel through which oxygen is delivered to the patient. The exhaled breath may freely flow through the airway channel towards a sampling port connected to the capnograph. The oxygen channel may be formed along a side of the insertion channel for patient comfort. Alternatively, the oxygen channel may be positioned in the bite block in any manner which permits high oxygen delivery, the distance between the airway channel and the oxygen channel preferably not less than the distance between the airway channel and the insertion channel.

In some embodiments of the invention, the bite block comprises an extendable oral nasal cannula, which is substantially maintained inside the patient's nostrils generally independent of the patient's head position and of movement of the bite block. The airway channel opens into a cavity in a forward section of the bite block, external to the patient's mouth. An oral prong in the oral nasal cannula is adapted to slide in a generally lateral direction along a z-axis back and forth along the cavity, and to rotate and tilt relative to a y-axis substantially perpendicular to the direction of sliding, in order to compensate for movement of the bite block relative to the patient's mouth. Additionally, the oral prong is adapted to slidingly extend in and out of an oral prong extension in a generally vertical direction along the y-axis substantially extending the length of the oral prong. A large degree of freedom of movement in the oral prong, and thereby in the oral nasal cannula, substantially reduces the possibility that the nasal prong may slip out of the bite block due to movement of the bite block relative to the patient's mouth. As a result, substantially continuous flow of exhaled breath is maintained to the capnograph. In some embodiments of the invention, the bite block comprises an airway channel which includes an opening to which the oral prong is affixed. Exhaled breath may then flow through the opening in the airway channel into the oral prong. In some embodiments of the invention, the bite block may include an oral prong as an integral part of the bite block. The oral prong may be connected to one or more nasal prongs. The integral oral prong may open into a roof of the airway channel.

In addition, according to some embodiments, the device and system may be adjustable to fit different patients.

In accordance with an embodiment of the invention, there is provided a bite block comprising an insertion channel and an airway channel, wherein the airway channel is adapted to pass substantially free flow of breath, and wherein the insertion channel is adapted to pass substantially free flow of breath and to pass a medical instrument. Optionally, a portion of the airway channel opens into a cavity adapted to receive an oral prong, wherein the oral prong is adapted to sample breath from a patient. Optionally, the cavity is further adapted to allow relative motion between the bite block and the prong without substantially reducing the breath sampling.

In accordance with some embodiments of the invention, the airway channel is adapted to receive an oral prong, wherein the oral prong is adapted to sample breath from a patient.

In accordance with some embodiments of the invention, the airway channel is adapted to pass substantially free flow of breath through a duct. Optionally, the duct is further adapted to enable a viewer to view the position of an oral prong functionally connected to the bite block.

In accordance with some embodiments of the invention, the bite block further comprises an oxygen channel located in proximity to the insertion channel, wherein the oxygen channel is adapted to direct oxygen towards the inside of the mouth of a patient. Optionally, the airway channel is adapted to protrude further into the back of the mouth relative to the insertion channel and/or the oxygen channel. Additionally or alternatively, the bite block is adapted to reduce the flow of oxygen from the oxygen channel into the airway channel, such that the oxygen pressure is adapted to be lower than the opposing pressure created by the exhaled breath, so that the exhaled breath can push back out of the mouth the oxygen, and at least partially prevent oxygen from reaching the airway channel opening and consequently diluting the sampled breath.

In accordance with an embodiment of the invention, there is provided a bite block comprising an airway channel, wherein the airway channel is adapted to pass substantially free flow of breath and wherein a portion of the airway channel opens into a cavity adapted to receive an oral prong for sample breath from a patient. The cavity is further adapted to allow relative motion between the bite block and the prong without substantially reducing the breath sampling. Optionally, the bite block further comprises an insertion channel adapted to pass substantially free flow of breath, and to pass a medical instrument.

In accordance with some embodiments of the invention, the airway channel is adapted to pass substantially free flow of breath through a duct. Optionally, the duct is further adapted to enable a viewer to view the position of an oral prong functionally connected to the bite block.

In accordance with some embodiments of the invention, the bite block further comprises an oxygen channel located in proximity to the channel, wherein the oxygen channel is adapted to direct oxygen towards the inside of the mouth of a patient. Optionally, the airway channel is adapted to protrude further into the back of the mouth relative to the insertion channel and/or said oxygen channel. Additionally or alternatively, the bite block is adapted to reduce the flow of oxygen from the oxygen channel into the airway channel, such that the oxygen pressure is adapted to be lower than the opposing pressure created by the exhaled breath, so that the exhaled breath can push back out of the mouth the oxygen, and at least partially prevent oxygen from reaching the airway channel opening and consequently diluting the sampled breath.

In accordance with an embodiment of the invention, there is provided a system for sampling breath, the system comprising: a bite block comprising an insertion channel and an airway channel, wherein the airway channel is adapted to pass substantially free flow of breath, and wherein said an insertion channel is adapted to pass substantially free flow of breath and to pass a medical instrument; and a valve adapted to regulate oxygen delivery to the oxygen channel.

In accordance with some embodiments of the invention, the airway channel opens into a cavity adapted to receive an oral prong, wherein the oral prong is adapted to sample breath from a patient. Optionally, the cavity is further adapted to allow relative motion between the bite block and the prong without substantially reducing the breath sampling.

In accordance with some embodiments of the invention, the airway channel is adapted to receive an oral prong, wherein the oral prong is adapted to sample breath from a patient. Optionally, the airway channel is adapted to pass substantially free flow of breath through a duct. Additionally, the duct is further adapted to enable a viewer to view the position of an oral prong functionally connected to said bite block.

In accordance with some embodiments of the invention, the system further comprises an oxygen channel located in proximity to the insertion channel, wherein the oxygen channel is adapted to direct oxygen towards the inside of the mouth of a patient. Optionally, airway channel extends further into the mouth relative to the insertion channel and/or the oxygen channel.

In accordance with some embodiments of the invention, there is provided a system for sampling breath, the system comprising: a bite block comprising an airway channel, wherein the airway channel is adapted to pass substantially free flow of breath and wherein a portion of the airway channel opens into a cavity adapted to receive an oral prong for sampling breath from a patient, the cavity is further adapted to allow relative motion between said bite block and said prong without substantially reducing the breath sampling; and a valve adapted to regulate oxygen delivery to said oxygen channel. Optionally, the system further comprising an insertion channel adapted pass substantially free flow of breath and to pass a medical instrument.

In accordance with an embodiment of the invention, there is provided a system for sampling breath, the system comprising: a bite block comprising an insertion channel and an airway channel, wherein the airway channel is adapted to pass substantially free flow of breath and wherein the insertion channel is adapted to pass substantially free flow of breath and to pass a medical instrument; and an oral nasal cannula adapted to sample breath.

BRIEF DESCRIPTION OF FIGURES

Examples illustrative of embodiments of the invention are described below with reference to figures attached hereto. In the figures, identical structures, elements or parts that appear in more than one figure are generally labeled with a same numeral in all the figures in which they appear. Dimensions of components and features shown in the figures are generally chosen for convenience and clarity of presentation and are not necessarily shown to scale. The figures are listed below.

DETAILED DESCRIPTION

Figure 1:
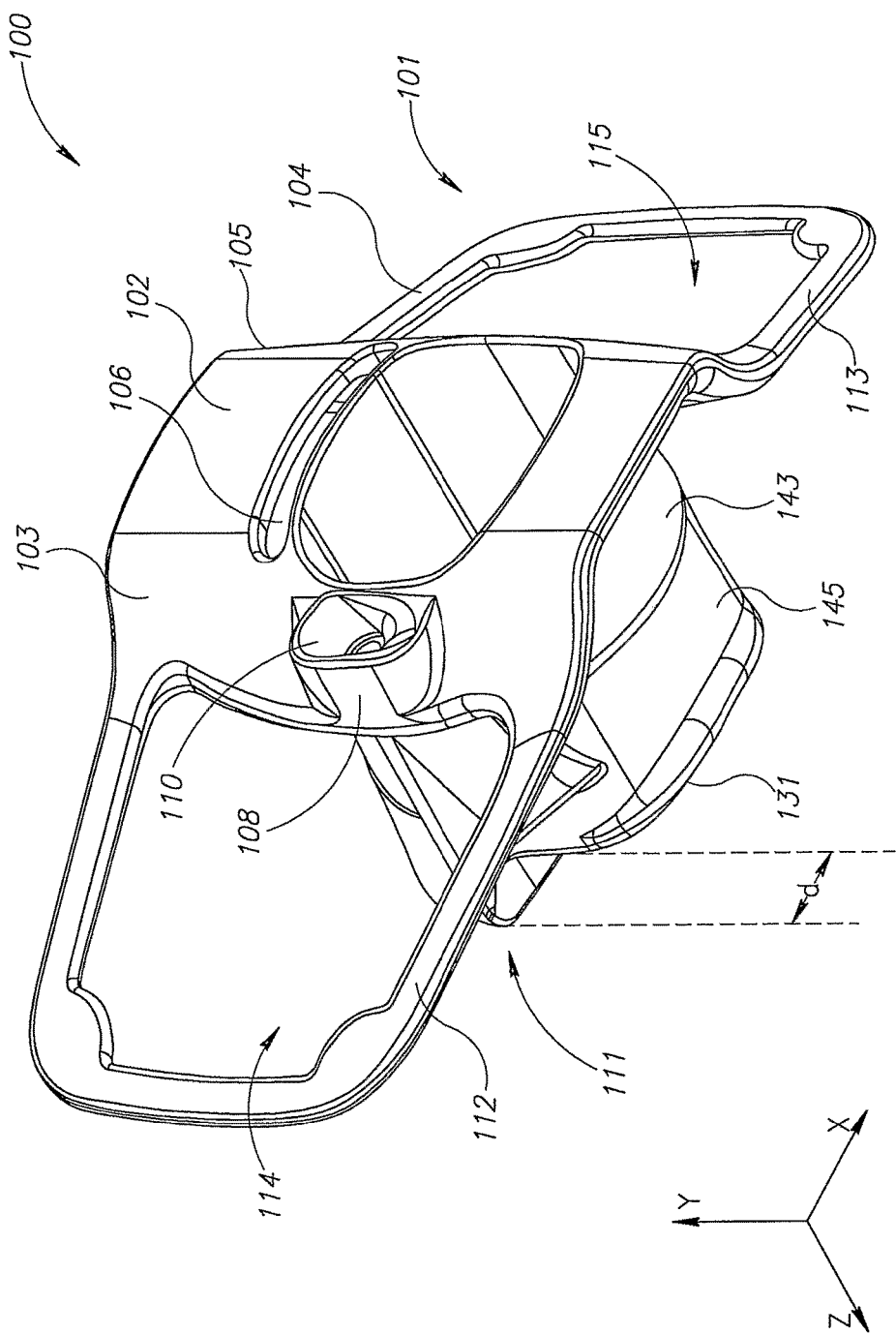
FIG. 1 schematically shows an isometric front view of an exemplary bite block adapted for capnography and oxygen delivery to a patient, in accordance with an embodiment of the invention.
Figure 2:
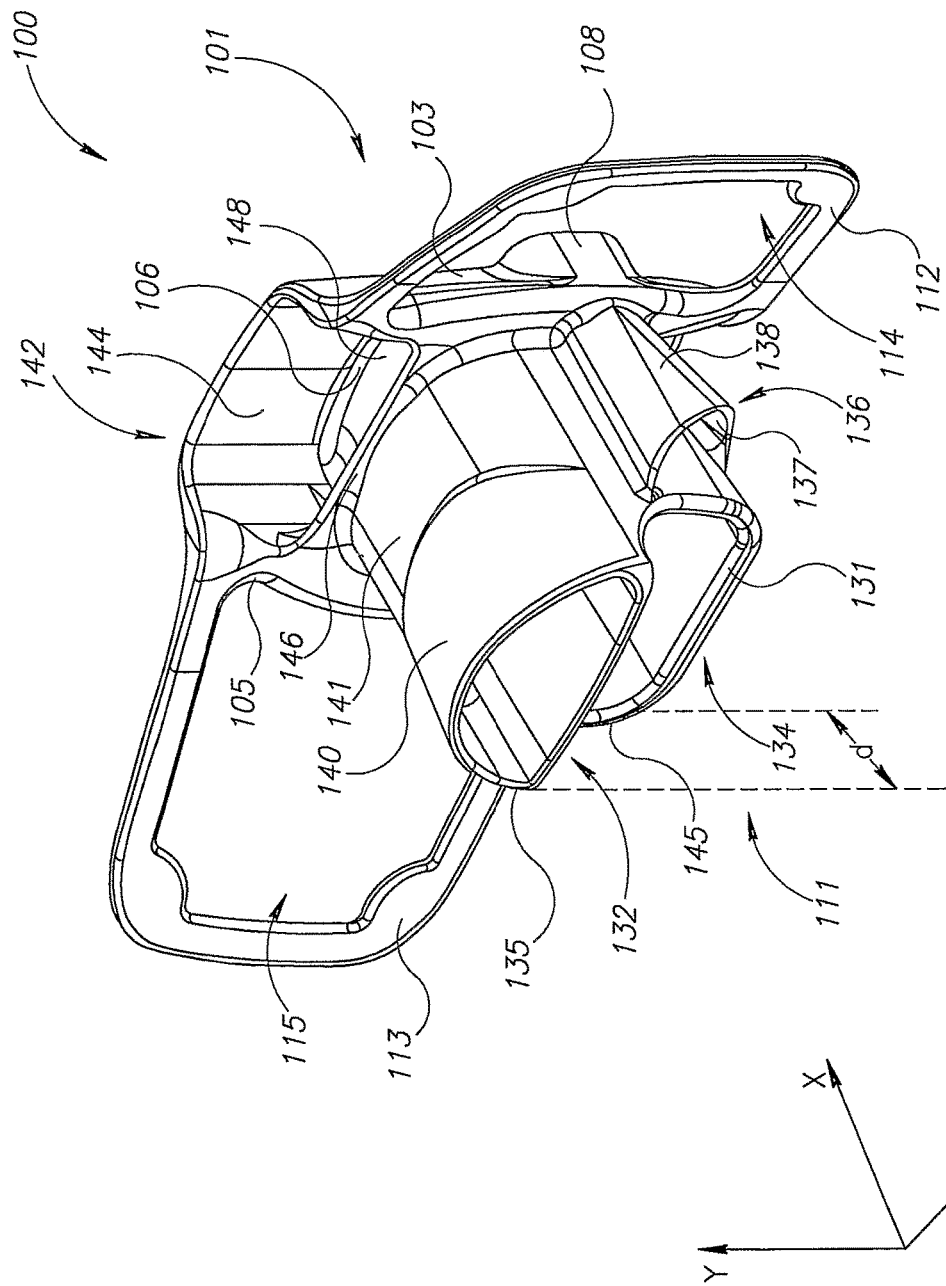
FIG. 2 schematically shows an isometric back view of the exemplary bite block in FIG. 1 in accordance with an embodiment of the invention.

Reference is made to FIGS. 1 and 2 which schematically show an isometric front view and back view, respectively, of an exemplary bite block 100 adapted for passing a medical instrument, perform capnography and if required, deliver oxygen to a patient, in accordance with an embodiment of the invention. Bite block 100 comprises an external section 101 and an oral insert, which may be refereed to as a mouthpiece 111. Mouthpiece 111 is adapted to be placed inside a patient's mouth, while external section 101 is configured to be fitted over the mouth and to substantially restrict movement of the mouthpiece inside the patient's mouth. External section 101 comprises a main body portion 102, which includes an opening 104 to an insertion channel 134. Insertion channel 134 is adapted to receive a medical instrument, for example an endoscope, which is inserted through opening 104 and extends through insertion channel 134 into a patient's mouth. Main body portion 102 comprises a first lateral section 103 which laterally extends from one side of main body portion 102 towards a first attachment 112. On the other side of main body portion 102, a second lateral section 105 laterally extends towards a second attachment 113. First attachment 112 and second attachment 113 comprise openings 114 and 115, respectively, the attachments adapted to receive a strap, or some other means of fixing the bite block to a patient's mouth, generally by attaching the strap, or other means, around the back of the head of the patient. Optionally, more than one strap or other means of attachment may be used to fix the bite block to the patient's mouth.

Mouthpiece 111 comprises insertion channel 134, an airway channel 132 and an oxygen channel 136. Insertion channel 134 extends from opening 104 along a major portion of the length of the mouthpiece to an end opening 131. Insertion channel 134 is formed by a surface 145 which is usually supported by the tongue when the mouthpiece is inserted in the patient's mouth, and a surface 143 which provides a biting surface for the patient's lower teeth. Surfaces 145 and 143 are contoured with rounded edges to substantially reduce any possible harm to the patient's mouth and/or tongue, and/or patient discomfort, typically associated with sharp edges.

Protruding from first lateral section 103 is an oxygen tube adapter 108, adapted to receive an oxygen tube for orally administering oxygen to the patient. Alternatively, oxygen tube adapter 108 may protrude from second lateral section 105. Optionally, the oxygen tube adapter may protrude from first lateral section 103 and second lateral section 105, or from other parts of bite block 100. Oxygen channel 136 extends from oxygen tube adapter 108 laterally along a length of insertion channel 134. Oxygen channel 136 is adapted to conduct oxygen flowing into oxygen tube adapter 108 through an opening 110, and through aperture 137 at the other end of oxygen channel 136, into the mouth of the patient. Optionally, oxygen channel 136 may extend the whole length of insertion channel 134. Oxygen channel 136 is formed by a substantially curved surface 138 to reduce any possible harm to the patient's mouth and/or tongue, and/or patient discomfort, typically associated with sharp edges. In accordance with an embodiment of the invention, aperture 137 is of a relative large diameter, generally in the range of 0.5-20 mm, for example, 2 mm, 3 mm, 5 mm, 8 mm, 12 mm, 15 mm, 18 mm, adapted to create a pressure decrease in the oxygen flow when flowing out of oxygen channel 136 into the mouth of the patient. Optionally, oxygen channel 136 may include more than one aperture. Additionally or alternatively, oxygen channel 136 may comprise one or more apertures, such as aperture 137 in insertion channel 134 through which oxygen, or optionally a portion of the delivered oxygen, may flow out of the oxygen channel into the patient's mouth.

In accordance with an embodiment of the invention, airway channel 132 is adapted to receive exhaled breath from the patient and to allow exhaled breath and inhaled air to flow freely back and forth along the channel. The exhaled breath free flows along airway channel 132 in the direction of a cavity 142, included in the forward section of the airway channel. Airway channel 132 extends from cavity 142 in a direction inwardly, or deeper, into the mouth of the patient a distance d compared to insertion channel 134. The distance d is measured in a direction along an x-axis from an opening 135 comprised in airway channel 132 to opening 131 and generally ranges from 5 mm-20 mm, for example 5 mm, 8 mm, 12 mm, 16 mm, 20 mm. In accordance with an embodiment of the invention, the pressure of the oxygen at opening 135 of airway channel 132 is less than the pressure of the opposing exhaled breath and therefore, oxygen is substantially prevented from entering airway channel 132 and diluting the exhaled breath.

Airway channel 132 is formed by a substantially curved surface 140 which may slope upwards in the direction of the roof of the mouth when the mouthpiece is inserted in the patient's mouth, and substantially curved surface 141 which provides a biting surface for the patient's upper teeth. Upward sloping of surface 140 allows for a larger opening 135 in airway channel 132 much like a funnel, opening 135 adapted to capture relatively large amounts of exhaled breath. The funnel design of airway channel 132, provided by sloping surface 140, provides for substantial free flow of breath in the airway channel. Surfaces 140 and 141 are contoured with rounded edges to substantially reduce any possible harm to the patient's mouth and/or to reduce patient discomfort, typically associated with sharp edges. In some embodiments of the invention, an opening may extend, partially or entirely, along the length between airway channel 132 and insertion channel 134.

In accordance with an embodiment of the invention the dimensions of cavity 142 are such that they allow an oral nasal cannula (not shown) to move, relative to bite block 100, linearly inside the cavity along the x-axis and/or y-axis and and/or z-axis, and/or angularly about the x and/or y and/or z axis, Relative motion of the oral nasal cannula substantially compensates for movement of bite block 100 relative to a patient's mouth, allowing oral nasal cannula to remain inserted in cavity 142 generally at all times. Cavity 142 is formed from a substantially vertical inner surface 144 of a section of main portion 102, a section of first lateral section 103, and a section of second lateral section 105. A border 146 perpendicularly extends from surface 141 at the border of the airway channel 132 with cavity 142, and generally serves to demarcate the border between the mouthpiece and the external section. A cavity floor 148 comprises a surface adapted to support the oral nasal cannula when fitted into the cavity. Cavity 142 further comprises a duct 106 in inner surface 144 adapted to allow exhaled breath and inhaled air to flow freely in and out of airway channel 132. Duct 106 may also be used by a viewer to view the position of the oral nasal cannula inside the cavity.

Figure 3:
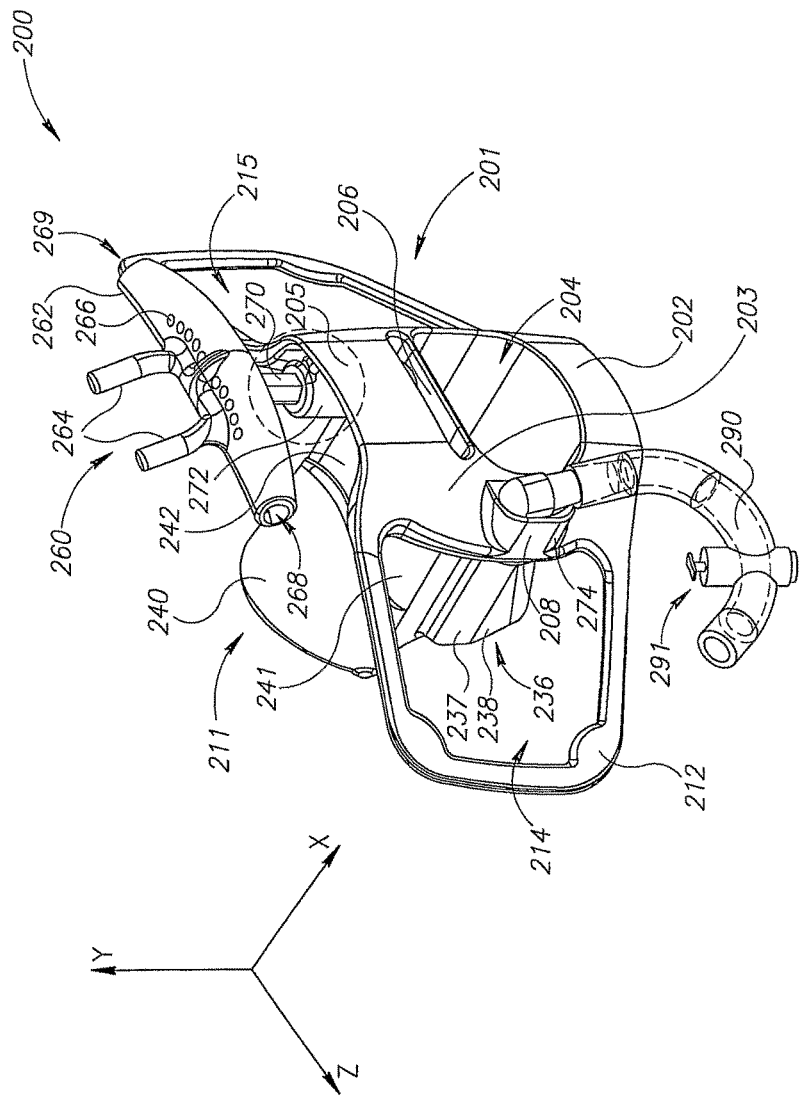
FIG. 3 schematically shows an isometric front view of an exemplary bite block comprising an oral nasal cannula and an oxygen tube.
Figure 4:
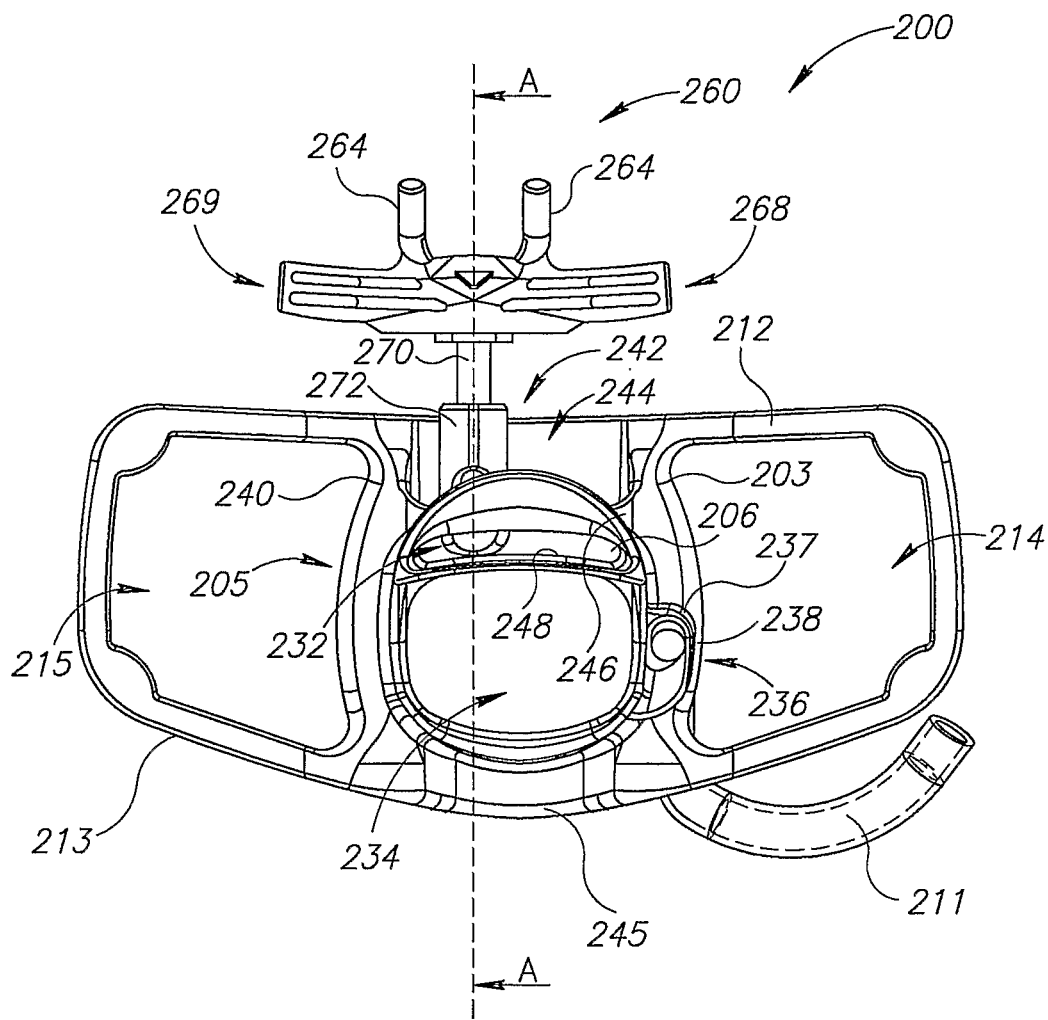
FIG. 4 schematically shows an back view of the exemplary bite block in FIG. 3 in accordance with an embodiment of the invention.
Figure 5:
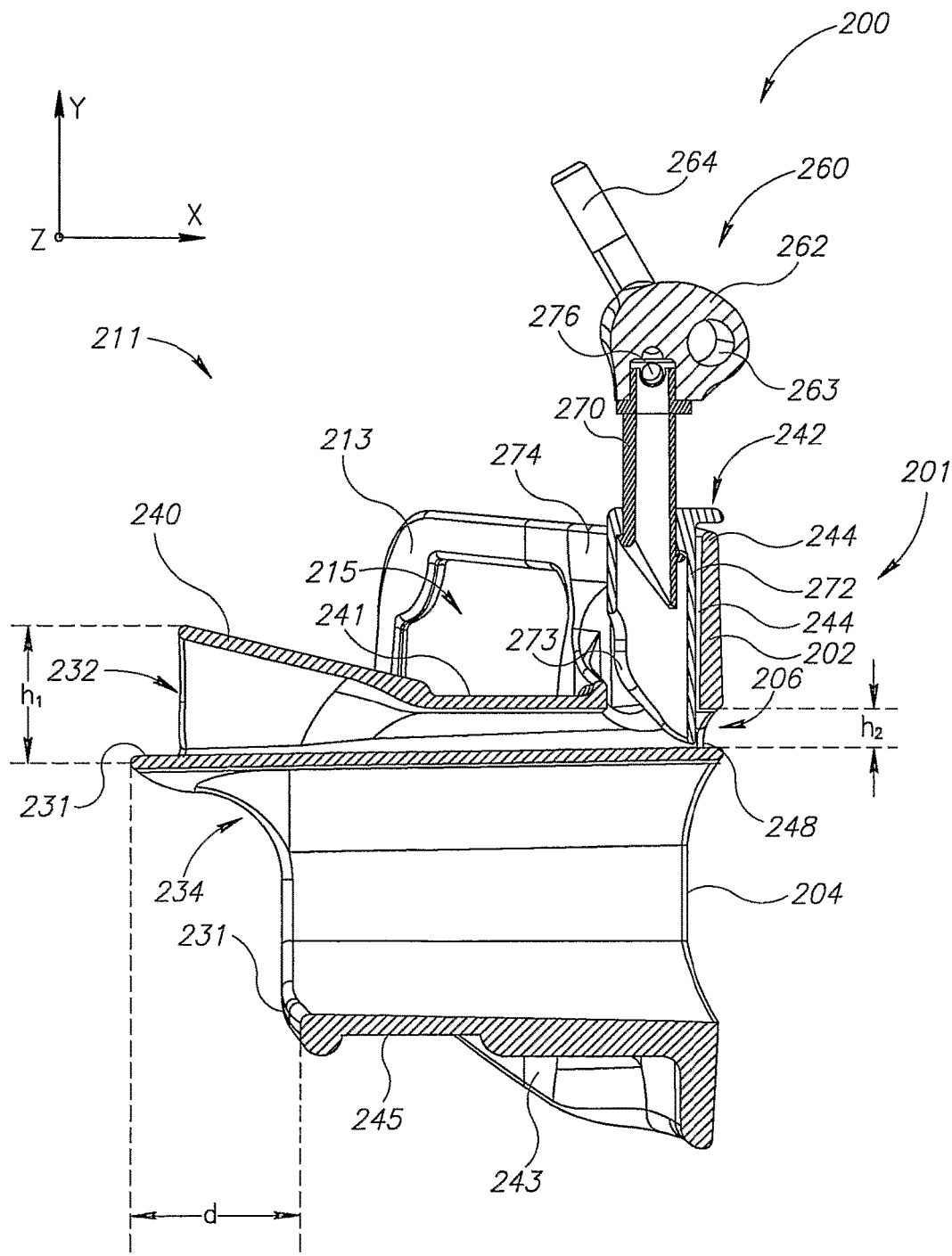
FIG. 5 schematically shows a cross-sectional view A-A of the exemplary bite block of FIG. 3, in accordance with an embodiment of the invention.

Reference is made to FIG. 3 which schematically shows an isometric front view of an exemplary bite block comprising an oral nasal cannula and an oxygen tube, to FIG. 4 which schematically shows a back view of the exemplary bite block in FIG. 3, and to FIG. 5 which schematically shows a cross-sectional view A-A of the exemplary bite block of FIG. 3 and FIG. 4, in accordance with an embodiment of the invention.

Bite block 200 is the same or substantially similar to bite block 100 shown in FIGS. 1 and 2, additionally comprising an oral nasal cannula 260 positioned inside cavity 242 and an oxygen tube 290, including a valve 291, attached to the bite block at an oxygen tube adapter 208. Bite block 200 comprises an external section 201, a mouthpiece 211, a main body portion 202, an opening 204, an insertion channel 234, a first lateral section 203, a first attachment 212, a second lateral section 205, a second attachment 213, openings 214 and 215, an airway channel 232, an oxygen channel 236, an end opening 231, a surface 245, a surface 243, oxygen channel 236, a curved surface 238, a cavity 242, an opening 235, a curved surface 240, a curved surface 241, a vertical inner surface 244, a border 246, a cavity floor 248, and a duct 206, all the same or substantially similar to that shown in FIGS. 1 and/or 2 at 101, 111, 102, 104, 134, 103, 112, 105, 113, 114, 115, 132, 136, 131, 145, 143, 136, 138, 142, 135, 140, 141, 144, 146, 148, and 106. It may be appreciated from FIG. 5 that curved surface 240 is a sloping surface extending from opening 231 to intersect curved surface 241, such that a height h1 of airway channel 232 is a maximum at opening 231 and decreases to a height h2 at the intersection with surface 241. The relatively large opening in airway channel 232 allows for better collection of orally exhaled breath from the patient. Height h1 of airway channel 232 is generally limited by the structure of the mouth and is typically in a range of 5-25 mm, for example, 10 mm, 14 mm, 16 mm, or 20 mm. Height h2 of airway channel 232 is generally limited by the size of the bite, and is typically in a range of 1-10 mm, for example, 2 mm, 3.5 mm, or 5 mm. Optionally, heights h1 and h2 may be the same.

Oxygen tube 290 is connected to bite block 200 by means of a rotational nipple 274 which is inserted into oxygen tube adapter 208. Optionally, rotational nipple 274 is a fixed nipple not adapted for rotational motion. Oxygen, or some other type of breathable gas, is delivered to the bite block through oxygen tube 290. The gas flows through the nipple into oxygen tube adapter 208 and through oxygen channel 236 into a patient's mouth.

Valve 291 is adapted to regulate oxygen flow in the direction of oxygen tube adapter 208 and oxygen channel 236, and in the direction of oral nasal cannula 260. Oxygen flow to oral nasal cannula 260 may be maintained, when bite block 200 is removed, through a nasal oxygen tube (not shown) extending from valve 291 to opening 268 in oral nasal cannula 260.

Oral nasal cannula 260 comprises a main body 262 from which extend two nasal prongs 264 adapted to be inserted into the patient's nostrils for exhaled breath collection. The exhaled breath from the patient's nostrils flows through the nasal prongs into a breath conduit 276. Breath conduit 276 leads through main body 262 to an exit opening 269 to which a breath sampling tube may be connected for delivering the exhaled breath to a capnograph.

Main body 262 further comprises oxygen delivery holes such as, for example hole 266, through which oxygen, or some other breathable gas, flows out of the main body into the patient's nostrils. The oxygen is delivered to the oral nasal cannula through a nasal oxygen tube which connects to opening 268 at one end of the main body. Opening 268 leads to a conduit 263 in main body 262 through which the oxygen flows to the oxygen delivery holes. Alternatively, opening 268 leads to a conduit 263, through which oxygen may flow into prongs (not shown).

An oral prong 270 comprising a hollow tube with a cut-away tip 274 is attached to the bottom side of main body 262. In accordance with an embodiment of the invention oral prong 270 comprises a hollow oral prong extension 272 into which the oral prong may be slidingly inserted into and retracted from, substantially extending the length of the oral prong when fully retracted. Optionally, oral prong 270 and oral prong extension 272 are fixed with respect to one another. Oral prong extension 272, comprises a hollow tube with a cut-away tip 273, and is adapted to be inserted into cavity 242.

Oral prong 270 is usually positioned in cavity 242 in a vertical position along a y-axis, supported by an extended abutment of oral prong extension 272 with inner surface 244, and by an abutment of cut-away tip 273 with cavity surface 248. Oral prong 270 is generally oriented such that an opening in cut-away tip 273 faces in the direction of airway channel 232. In accordance with an embodiment of the invention, oral prong 270 is adapted to sample the breath of a patient in airway channel 232. Orally exhaled breath flowing through airway channel 232 may flow with ease into oral prong extension 272 through cut-away tip 273, and into oral prong 270 through cut-away tip 274. The orally exhaled breath flowing into oral prong 270 flows through the prong into conduit 276 in main body 262 where it may combine with exhaled breath from the patient's nostrils. The exhaled breath then flows out exit opening 269.

In accordance with an embodiment of the invention oral prong 270 is adapted to slide in a generally lateral direction, relative to bite block 200, along a z-axis back and forth along the cavity floor 248, and to rotate and tilt relative to the y-axis substantially perpendicular to the direction of sliding. A large degree of freedom in movement in oral prong 270, and thereby in oral nasal cannula 260, substantially compensates for movement of bite block 200 relative to a patient's mouth, allowing oral nasal cannula 260 to remain inserted in cavity 242 generally at all times. In some embodiments of the invention, bite block 200 comprises an airway channel 232 which includes an opening to which oral prong 270 is affixed. Exhaled breath may then flow through the opening in airway channel 232 into oral prong 270.

In the description and claims of embodiments of the present invention, each of the words, "comprise" "include" and "have", and forms thereof, are not necessarily limited to members in a list with which the words may be associated.

The invention has been described using various detailed descriptions of embodiments thereof that are provided by way of example and are not intended to limit the scope of the invention. The described embodiments may comprise different features, not all of which are required in all embodiments of the invention. Some embodiments of the invention utilize only some of the features or possible combinations of the features. Variations of embodiments of the invention that are described and embodiments of the invention comprising different combinations of features noted in the described embodiments will occur to persons with skill in the art. The scope of the invention is limited only by the claims.

What we claim is:

1. A bite block comprising:
    a front plate configured to lodge against a patient's lips and forming a first opening and a second opening; and
    a mouthpiece configured for insertion into the patient's mouth, the mouthpiece comprising:
    an airway channel configured to receive exhaled breath from the patient and to allow exhaled breath and inhaled air to flow freely back and forth along the channel when in use, the airway channel extending from the second opening of the front plate to an airway channel end;
    an insertion channel extending away from the first opening to an end of the insertion channel, the insertion channel being formed by a wall having an inner surface and an external surface, wherein the insertion channel is configured to pass a medical instrument through the first opening and within the inner surface of the wall, wherein the insertion channel is positioned below a lower portion of the airway channel;
    a cavity orthogonal to and extending away from an upper portion of the airway channel and terminating in the upper portion of the airway channel at a location positioned between the second opening and the airway channel end; and
    an oxygen channel extending along at least a part of the external surface of the wall, wherein the external surface of the wall defines at least a portion of an interior surface of the oxygen channel and a portion of an exterior wall of the mouthpiece, wherein the wall completely separates the oxygen channel from the insertion channel such that there is no fluid communication between the oxygen channel and the insertion channel along the wall, and wherein the oxygen channel is configured to deliver oxygen therethrough, wherein the airway channel is formed external to the inner surface of the wall, such that the airway channel is separated from the insertion channel and the oxygen channel, and wherein the airway channel is configured to protrude further into the patient's mouth than the oxygen channel and the insertion channel when in use, such that a distance is maintained between the airway channel end and the end of the insertion channel.

2. The bite block of claim 1, wherein the airway channel is formed by a first substantially curved surface which slopes upwards in the direction of the roof of the patient's mouth when the mouthpiece is inserted in the patient's mouth, and a second substantially curved surface, which is configured to provide a biting surface for the patient's upper teeth.

3. The bite block of claim 1, wherein the oxygen channel is slanted downwards so that oxygen at least partially is prevented from reaching the airway channel end and consequently diluting the sampled breath.

4. The bite block of claim 1, wherein the cavity is positioned in a forward section of the bite block and configured so as to be external to the patient's mouth when in use, the cavity configured to facilitate sampling of exhaled breath therefrom, when an oral prong is present in the cavity, and to allow ambient air and exhaled breath to flow in and out of the airway channel in the presence of the oral prong in the cavity.

5. The bite block of claim 4, wherein the oral prong comprises a third opening configured to face towards the flow of breath flowing along the airway channel.

6. The bite block of claim 4, wherein the cavity is further configured to allow relative lateral movement between the oral prong and the cavity, while maintaining the third opening of the oral prong facing towards the flow of breath flowing along the airway channel.

7. The bite block of claim 6, wherein the second opening allows exhaled breath and inhaled air to flow substantially freely back and forth along the airway channel.

8. The bite block of claim 7, wherein the second opening is further adapted to enable a viewer to view the position of the oral prong functionally connected to the bite block.

9. The bite block of claim 1, wherein the insertion channel comprises at least one aperture, the aperture being in the wall of the insertion channel between the first opening and an end opening thereof, and wherein the oxygen channel is configured to deliver oxygen into the insertion channel through the at least one aperture, such that oxygen enters the insertion channel prior to the end opening thereof, thereby substantially preventing oxygen from the oxygen channel from entering the airway channel when in use.

10. The bite block of claim 9, wherein the aperture is of a diameter configured to reduce the oxygen pressure to be lower than the opposing pressure created by the exhaled breath, so that oxygen at least partially is prevented from reaching the airway channel opening and consequently diluting the sampled breath.

11. A system for sampling breath, the system comprising a bite block comprising:
a front plate configured to lodge against a patient's lips; and
a mouthpiece configured for insertion into the patient's mouth, wherein the mouthpiece comprises:

an airway channel configured to receive exhaled breath from a patient and to allow exhaled breath and inhaled air to flow freely back and forth along the airway channel when in use; and terminating in a duct opening formed through the front plate;

an insertion channel extending from a first opening of the insertion channel formed through the front plate along the mouthpiece, the insertion channel formed by a wall having an inner surface and an external surface, wherein the insertion channel is configured to pass a medical instrument within the inner surface of the wall;

an oxygen channel, wherein the oxygen channel is formed adjacent to the insertion channel such that the oxygen channel extends along at least a part of the external surface of the wall of the insertion channel, wherein the external surface defines at least a portion of an interior surface of the oxygen channel and a portion of an exterior wall of the mouthpiece, wherein the wall completely separates the oxygen channel from the insertion channel such that there is no fluid communication between the oxygen channel and the insertion channel along the wall the oxygen channel is configured to deliver oxygen therethrough, wherein the airway channel is configured to protrude farther into the patient's mouth than the oxygen channel and the insertion channel when in use, such that a substantial distance is maintained between respective internal ends of the airway channel and the insertion channel.

12. The system of claim 11, wherein the airway channel is formed by a first substantially curved surface which slopes upwards in the direction of the roof of the patient's mouth when the mouthpiece is inserted into the patient's mouth, and a second substantially curved surface, which is configured to provide a biting surface for the patient's upper teeth.

13. The system of claim 11, wherein the oxygen channel is slanted downwards so that oxygen at least partially is prevented from reaching the airway channel and consequently diluting the sampled breath.

14. The system of claim 11, further including a cavity positioned in a forward section of the bite block and configured so as to be external to the patient's mouth when in use, the cavity is configured to facilitate sampling of exhaled breath therefrom, when an oral prong is present in the cavity, and to allow ambient air and exhaled breath to flow in and out of the airway channel in the presence of the oral prong in the cavity.

15. The system of claim 14, wherein the cavity is further configured to allow relative lateral movement between the oral prong and the cavity, while maintaining an opening of the oral prong facing towards the flow of breath flowing along the airway channel.

16. The system of claim 11, wherein the insertion channel comprises at least one aperture, the aperture being in a wall of the insertion channel between the first opening and an end opening thereof, and wherein the oxygen channel is configured to deliver oxygen into the insertion channel through the at least one aperture, such that oxygen enters the insertion channel prior to the end opening thereof, thereby substantially preventing oxygen from the oxygen channel from entering the airway channel when in use.

17. The system of claim 16, wherein the aperture is of diameter configured to reduce the oxygen pressure to be lower than the opposing pressure created by the exhaled breath, so that oxygen at least partially is prevented from reaching the airway channel and consequently diluting the sampled breath.

18. The system of claim 11, further including a valve configured to regulate oxygen delivery from being supplied through to the oxygen channel to being supplied through an oral/nasal cannula such that, when in use, oxygen flow can be maintained, when the bite block is removed.

* * * * *